United States Patent [19]

McCarthy et al.

[11] Patent Number: 5,177,261
[45] Date of Patent: Jan. 5, 1993

[54] SYNTHESIS OF IOVERSOL USING CHLOROACETYL CHLORIDE

[75] Inventors: William Z. McCarthy, St. Louis; Mills T. Kneller, University City; Youlin Lin, Chesterfield; David H. White, Ballwin, all of Mo.

[73] Assignee: Mallinckrodt Medical, Inc., St. Louis, Mo.

[21] Appl. No.: 733,946

[22] Filed: Jul. 22, 1991

[51] Int. Cl.⁵ ............................................ C07C 233/64
[52] U.S. Cl. ......................................... 564/153; 424/5
[58] Field of Search ............................. 564/153; 424/5

[56] References Cited

U.S. PATENT DOCUMENTS 4,396,598  8/1983  Lin ........................................ 424/5

Primary Examiner—Richard L. Raymond
Assistant Examiner—Shailendra Kumar
Attorney, Agent, or Firm—Rita D. Vacca

[57] ABSTRACT

The use of chloroacetylchloride as an alternative or substitute reagent for acetoxychloride in the synthesis of N,N'- bis (2,3-dihydroxypropyl)-5-N-(2-hydroxyethyl)glycolamido-2,4,6-triiodoisophthalamide.

13 Claims, No Drawings

SYNTHESIS OF IOVERSOL USING CHLOROACETYL CHLORIDE

FIELD OF THE INVENTION

The present invention relates to the use of chloroacetyl chloride as an alternative or substitute reagent for acetoxyacetylchloride in the synthesis of Ioversol.

BACKGROUND OF THE INVENTION

Ioversol is disclosed as a useful nonionic x-ray contrast agent in U.S. Pat. No. 4,396,598. 5-acetoxyacetamido-N,N'-bis(2,3-diacetoxypropyl)-2,4,6-triiodoisophthalamide having the following structure:

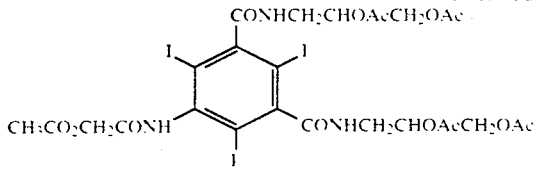

FORMULA I is an intermediate compound in the production of Ioversol. The compound of Formula I and its use in the production of ioversol is likewise disclosed in U.S. Pat. No. 4,396,598 incorporated herein by reference. 5-acetoxyacetamido-N,N'-bis(2,3-diacetoxypropyl)-2,4,6-triiodoisophthalamide, as disclosed in U.S. Pat. No. 4,396,598, may be produced by adding acetoxyacetylchloride (AAC) to a N,N-dimethylacetamide solution of a compound of the following structure:

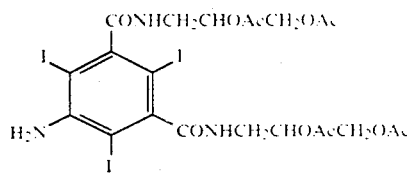

FORMULA II and stirring until the reaction is complete. The reaction mixture is then diluted with 1,1,2-trichloroethane and extracted with aqueous sodium bicarbonate solutions and aqueous sodium chloride solutions.

The dilution procedure using 1,1,2-trichloroethane may alternatively be carried out using an organic solvent such as, but not limited to, carbon tetrachloride, dichloromethane, chloroform, 1,2-di-chloroethane, 1,1,2-trichloroethylene, 1,1,2-trichloro-ethane, 1,1,1trichloroethane and tetrachloroethylene, but most preferably 1,1,2-trichloroethane.

The procedure for producing 5-acetoxyacetamidoN,N'-bis(2,3-diacetoxypropyl)-2,4,6-triiodoisophthalamide has become well known in the art and heretofore required the use of acetoxyacetyl chloride (AAC) for the intermediate synthetic step just described.

An improved procedure that eliminates the need for acetoxyacetyl chloride (AAC) in the intermediate synthetic step used to produce 5-acetoxyacetamido-N,N'-bis(2,3-diacetoxypropyl)-2,4,6-triiodoisophthalamide is desired as an alternate and/or a more cost efficient method of producing Ioversol. It is, therefore, an object of the present invention to meet these needs.

SUMMARY OF THE INVENTION

One method of producing ioversol without the use of acetoxyacetylchloride (AAC) begins with a solvent solution of 5-amino-N,N'-bis(2,3-diacetoxypropyl)-2,4,6-triiodoisophthal-amide(1). Compound 1 may be prepared for use in this reaction by distilling off some of the solvent to remove and/or reduce impurities, or alternatively, the solvent solution may be used directly without distillation. N,N-dimethylacetamide (DMAC) and chloroacetyl-chloride (CAC), which is an impurity found in AAC, are then added to the 5-amino-N,N'-bis(2,3-diacetoxypropyl)-2,4,6-triiodoisophthalamide(1) and the solution is stirred at 37° C. until the reaction is complete. Hydrochloric acid is produced as a waste product of this reaction. The DMAC present in the solution is mildly basic and thereby reacts with the hydrochloric acid generated to form a DMAC complex. After dilution with an organic solvent, the reaction solution is extracted with aqueous sodium bicarbonate solutions and aqueous sodium chloride solutions. The resulting 5-(chloroacetamido)-N,N'-bis(2,3-diacetoxypropyl)-2,4,6-triiodoisophthalamide(2)may be used without further purification as an intermediate in the production of N,N'-bis(2,3-dihydroxypropyl)-5-[N-(2-hydroxyethyl)glycolamido]-2,4,6-triiodoisophthalamide (Ioversol)(4) according to the reactions illustrated in Scheme 1 below. The final product, ioversol (4), produced through the use of CAC has an equivalent purity, approximately 95%, as that produced through the use of the more costly solvent AAC.

SCHEME 1

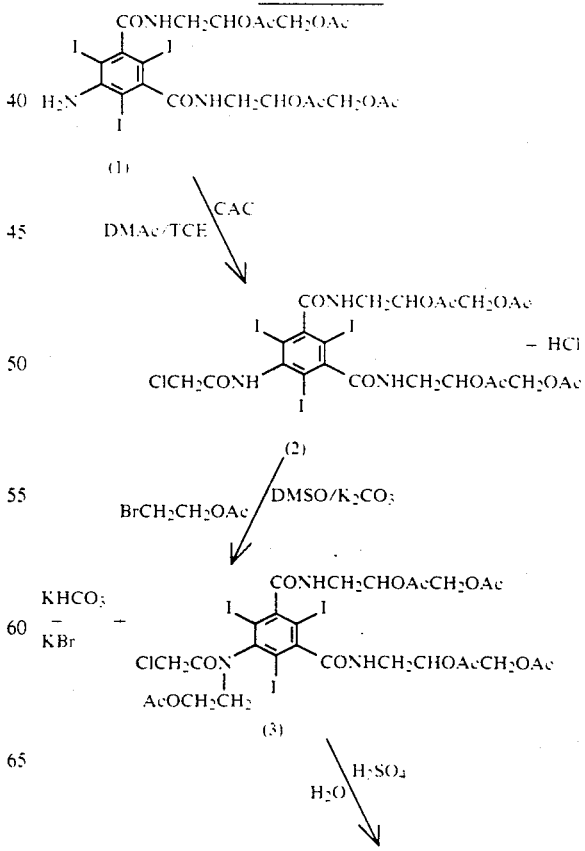

-continued

SCHEME 1

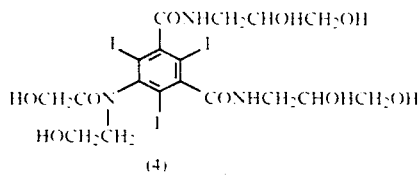

CAC = Chloroacetylchloride
DMAC = N,N-dimethylacetamide
TCE = 1,1,2-trichloroethane
DMSO = Dimethylsulfoxide Another method of producing ioversol using chloroacetylchloride (CAC) instead of acetoxyacetylchloride (AAC) uses dried 5-amino-N,N,bis(2,3-dihydroxypropyl)2,4,6-triiodoisophthalamide(5) which normally serves as a precursor to 5-amino-N,N,bis(2,3-diacetoxypropyl)-2,4,6-triiodoisophthalamide(1) in the ioversol process. Therefore, this particular method eliminates one step, the production of 5-amino-N,N,-bis(2,3-diacetoxypropyl)-2,4,6-triiodoisophthalamide(1), in the production of ioversol(4). This step-saving method begins by adding N,N-dimethylacetamide (DMAC) and chloroacetylchloride (CAC) to 5-aminoN,N'-bis(2,3-dihydroxypropyl)-2,4,6-triiodoisophthalamide (5) and stirring until the reaction is complete. (4-dimethylaminopyridine (DMAP) may also be used as a catalyst and added to compound (5) along with the DMAC and CAC although it is not necessary.) Hydrochloric acid is produced as a waste product of this reaction. After dilution with an organic solvent, the reaction solution is extracted with aqueous sodium bicarbonate solutions and aqueous sodium chloride solutions. The resulting pentachloro-derivative of 5-acetoxyacetamido-N,N,-bis(2,3-diacetoxypropyl)-2,4,6-triiodoisophthalamide(6) may be used without further purification in the production of N,N'-bis(2,3-dihydroxy-propyl)-5-[N-(2-hydroxyethyl)glycolamido]-2,4,6-triiodo-isophthalamide(Ioversol)(4) according to the reactions illustrated in Scheme 2 below.

SCHEME 2

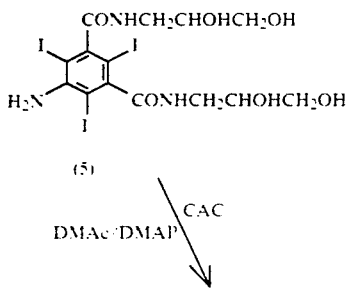

-continued

SCHEME 2

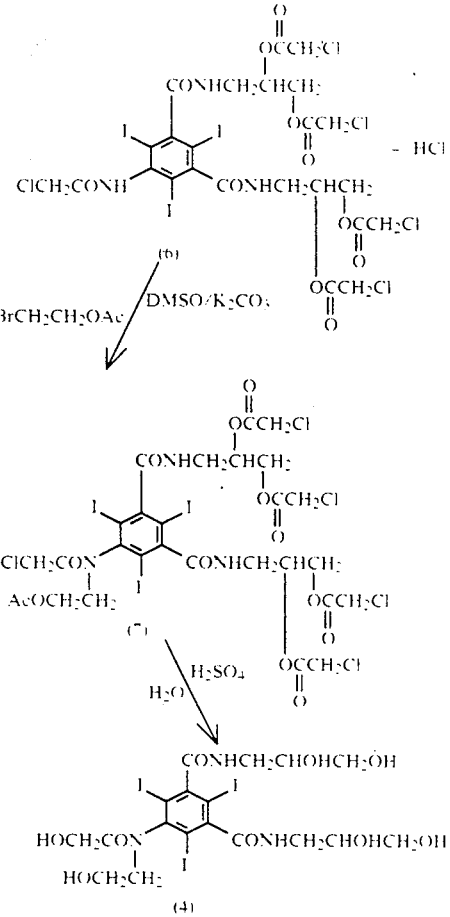

CAC = Chloroacetylchloride
DMAC = N,N-dimethylacetamide
DMAP = 4-dimethylaminopyridine
DMSO = Dimethylsulfoxide Both of the above-described processes have the advantage of eliminating the need for acetoxyacetyl chloride in the intermediate synthetic steps used in the production of N,N'-bis(2,3-dihydroxypropyl)-5-[N-(2-hydroxyethyl)glycolamido]-2,4,6-triiodoisophthalamide (Ioversol). Elimination of acetoxyacetyl chloride and substitution with chloroacetylchloride (CAC) is important to reduce the costs of production, to decrease impurities and to provide alternative routes of production for N,N'-bis(2,3-dihydroxypropyl)-5-[N-(2-hydroxyethyl)glycolamido]-2,4,6-triiodoisophthalamide(4). Additionally, the need for acetic anahydride is likewise eliminated through the process illustrated in Scheme 2 which reduces the cost of production even further.

DETAILED DESCRIPTION OF THE INVENTION 5-chloroacetamido-N,N'-bis(2,3-diacetoxypropyl)-2,4,6-triiodoisophthalamide(2) may be prepared according to the present invention by first distilling off some of the solvents from 5-amino-N,N,-bis(2,3-diacetoxypropyl)-2,4,6-triiodoisophthalamide(1) to reduce and/or remove any solvent impurities therefrom. This distillation of solvent(s) from compound 1 is optional. N,N-Dimethylacetamide (DMAC) and chloroacetylchloride (CAC), an impurity found in AAC, are then added to the previously distilled solution and stirred until the acylation reaction is complete. The solution which is highly viscous is then diluted to improve fluidity, and thereby ease workability, with an organic solvent such as for example toluene, a halocarbon solvent or a chlorocarbon solvent. Examples of such solvents include but are not limited to carbon tetrachloride, dichloromethane, chloroform, 1,2-dichloroethane, 1,1,2-trichloroethylene, 1,1,2-dichloroethane, 1,1,1-trichloroethane and tetrachloroethylene, but preferably 1,1,2-trichloroethane.

After dilution, the solvent is extracted with aqueous sodium bicarbonate solutions (preferably containing approximately 10–15% sodium bicarbonate) and/or aqueous sodium chloride solutions (preferably containing approximately 10–15% sodium chloride). This usually results in a mixture of 5-chloroacetamido-N,N'-bis(2,3-diacetoxypropyl)-2,4,6-triiodoisophthalamide(2) in 1,1,2-trichloroethane at approximately 25 to 30 percent solids. The resulting 5-chloroacetamido-N,N'-bis(2,3-diacetoxypropyl)-2,4,6-triiodoisophthalamide(2) may be used as an intermediate to produce N,N'-bis(2,3-dihydroxypropyl)-5-[N-(2-hydroxyethyl)glycolamido]-2,4,6-triiodoisophthalamide (Ioversol)(4) as illustrated in Scheme 1 above. The same is true for the production of N,N'-bis(2,3-dihydroxypropyl)-5-[N-(2-hydroxyethyl)glycolamido]-2,4,6-triiodoisophthalamide (Ioversol)(4) from 5-amino-N,N'-bis(2,3-dihydroxypropyl)-2,4,6-triiodoisophthalamide(5) stirred with chloroacetylchloride (CAC), N,N-dimethylacetamide (DMAC) and optionally 4-dimethylaminopyridine (DMAP). This reaction is likewise illustrated in Scheme 2 above.

The present invention as described above is further illustrated by the following examples, but is not intended to be limited thereby.

EXAMPLE 1

The Preparation of
5-chloroacetamido-N,N'-bis-(2,3-diacetoxypropyl)-
2,4,6-triiodoisophthalamide A solution of 5-amino-N,N'-bis(2,3-diacetoxypropyl)-2,4,6-triiodoisophthalamide (69.8 g) in 1,1,2-trichloroethane was prepared (total volume 177 ml). N,N-dimethylacetamide (DMAC) (17.4 ml) and chloroacetyl chloride (CAC) (18.1 g) were added to the reaction flask and the reaction was stirred until the reaction was complete. The reaction mixture was then diluted by approximately a factor of 3 with 1,1,2-trichloroethane (82 ml) and extracted with aqueous approximately 10% sodium bicarbonate solutions (313 ml:31 g NaHCO$_3$) and aqueous approximately 10% sodium chloride solutions (145 ml:14.5 g NaCl). The resulting solution of 5-chloroacetamido-N,N'-bis(2,3-diacetoxypropyl)-2,4,6-triiodoisophthalamide(2) is used as an intermediate in the production of ioversol without further purification.

EXAMPLE 2

The Preparation of 5-chloroacetamido-N,N-bis[2,-3di(chloroacetoxypropyl)]-2,4,6-triiodoisophthalamide
N,N-dimethylacetamide (75.2 ml), 4-dimethylaminopyridine (0.005 g moles, 0.61 g) and granular 5-amino-N,Nbis(2,3-dihydroxypropyl)-2,4,6-triiodoisophthalamide (0.1 g mole, 70.5 g) are placed into a 500 ml. 3-necked round bottomed flask. The mixture is stirred and heated to approximately 55° C. to dissolve the solids. Chloroacetylchloride (0.55 g mole, 62.1 g) is added slowly with stirring and the reaction temperature is controlled at 50°–70° C. After completing the addition, the reaction solution is allowed to stir at approximately 60° C. to complete the reaction, approximately 3 hr.

After the reaction is completed, 1,1,2-trichloroethane (TCE) is added (approximately 152 ml) diluting the solution by approximately a factor of 3 and the solution is stirred and cooled to approximately 20° C. Stirring and cooling are continued and aqueous sodium carbonate solution (approximately 0.6 moles, 52 g in a 13% w/v solution is slowly added to the stirred TCE solution at a rate which will maintain the temperature at less than 27° C. After stirring for 30 minutes, the reaction mixture containing TCE, DMAC, CAC, 5-amino-N,N-bis(2,3-dihydroxypropyl)-2,4,6-triiodoisophthalamide is transferred to a separatory funnel and the organic layer is separated from the aqueous layer. The organic layer is washed with a 10% w/v sodium chloride solution in a similar manner. The resulting TCE solution of the product is suitable for conversion to N,N-bis(2,3-dihydroxypropyl)-5-[N-(2-hydroxyethyl)glycolamido]-2,4,6-triiodoisophthalamide (Ioversol) as shown above.

The process of the present invention is less expensive, easier to perform and results in fewer impurities.

Accordingly, having described our invention, we claim:

1. A process for the production of ioversol [5chloroacetamido-N,N'-bis(2,3-diacetoxypropyl)-2,4,6triiodoisophthalamide] from 5-amino-N,N'-bis(2,3-diacetoxypropyl)-2,4,6-triiodoisophthalmaide, comprising the steps of:
   a. reacting N,N-dimethylacetamide, chloroacetylchloride and 5-amino-N,N'-bis(2,3-diacetoxypropyl)-2,4,6-triiodoisophthalamide to undergo a N-alkylation reaction to form an amide reaction mixture;
   b. diluting said amide reaction mixture with an organic solvent;
   c. extracting said amide reaction mixture with an aqueous solution to undergo a N-acylation reaction to recover 5-chloroacetamido-N,N'-bis(2,3-diacetoxypropyl)-2,4,6-triiodoisophthalamide, a N-alkyl, and
   d. hydrolyzing said N-alkyl to produce ioversol.

2. The process of claim 1, wherein said organic solvent is selected from a group consisting of carbontetrachloride, dichloromethane, chloroform, toluene, 1,2-dichloroethane, 1,1,2-trichloroethylene, 1,1,2-dichloroethane, 1,1,1-trichloroethane and tetrachloroethylene.

3. The process of claim 1, wherein said organic solvent is 1,1,2-trichloroethane.

4. The process of claim 1, wherein said aqueous solution is an aqueous sodium bicarbonate solution.

5. The process of claim 1, wherein said aqueous solution is an aqueous sodium chloride solution.

6. The process of claim 1, wherein said aqueous solution is an aqueous sodium bicarbonate solution.

7. The process of claim 1, wherein said 5-amino-N,N'-bis(2,3-diacetoxypropyl)-2,4,6-triiodoisophthalamide has solvent impurities reduced or removed therefrom by distilling off said solvent impurities.

8. A process for the production of ioversol comprising the steps of:
   a. reacting N,N-dimethylacetamide, chloroacetylchloride and 5-amino-N,N'-bis(2,3-dihydroxypropyl)-2,4,6-triiodoisophthalamide to undergo a N-acylation reaction to form a secondary amide reaction mixture;

b. diluting said secondary amide reaction mixture with an organic solvent;

c. extracting said secondary amide reaction mixture with an aqueous solution to recover 5-chloroacetamido-N,N'-bis[2,3-di(chloroacetoxypropyl)]-2,4,6-triiodoisophthalamide.

d. N-alkalizing 5-chloracetamide-N,N'-bis[2,3-di(-chloro-acetoxypropyl)]-2,4,6-triiodoisopthalamide to produce a N-alkyl mixture, and e. hydrolyzing said N-alkyl mixture to produce ioversol.

9. The process of claim 7, wherein said organic solvent is selected from group consisting of carbontetrachloride, dichloromethane, chloroform, toluene, 1,2-dichloroethane, 1,1,2-trichloroethylene, 1,1,2-dichloroethane, 1,1,1-trichloroethane and tetrachloroethylene.

10. The process of claim 7, wherein said organic solvent is 1,1,2-trichloroethane.

11. The process of claim 7, wherein said aqueous solution is an aqueous sodium chloride solution.

12. The process of claim 7, wherein said aqueous solution is an aqueous sodium bicarbonate solution.

13. The process of claim 7, wherein said aqueous solution is an aqueous sodium bicarbonate solution.

* * * * *

UNITED STATES PATENT AND TRADEMARK OFFICE
CERTIFICATE OF CORRECTION

PATENT NO. : 5,177,261
DATED : January 5, 1993
INVENTOR(S) : William Z. McCarthy, Mills T. Kneller, Youlin Lin, David H. White It is certified that error appears in the above-identified patent and that said Letters Patent is hereby corrected as shown below:

Column 2, line 13
  "N,N," should be --N,N'--;

Column 3, line 20
  "N,N," should be --N,N'--;

Column 3, line 21
  "dihydroxypropyl)" should be --dihydroxypropyl)- --;

Column 3, line 22
  "N,N," should be N,N'--;

Column 3, line 26
  "N,N," should be --N,N'--;

Column 3, line 31
  "5-amino N" should be --5-amino-N--;

Column 3, line 46
  "N,N," should be --N,N'--;

Column 4, line 53
  "hydroxyethyl)" should be --hydroxyethyl)- --;

UNITED STATES PATENT AND TRADEMARK OFFICE
CERTIFICATE OF CORRECTION

PATENT NO. : 5,177,261

DATED : January 5, 1993

INVENTOR(S) : William Z. McCarthy, Mills T. Kneller, Youlin Lin, David H. White

It is certified that error appears in the above-identified patent and that said Letters Patent is hereby corrected as shown below:

Column 4, line 63
"N,N," should be --N,N'--;

Column 5, lines 59, 60
"[2,3di should be --[2,3-di--;

Column 5, line 63
"N,Nbis" should be --N,N-bis--;

Column 6, lines 28, 29
"production of ioversol [5 chloroacetamido -N,N'-bis(2,3-diacetoxypropyl) -2,4,6 triiodoisophthalamide] from" should be --ioversol from--;

Column 6, line 30
"triiodoisophthalmaide" should be --triiodoiophthalamide--;

Column 6, line 43
"-bis(" should be -- -bis-(--;

Signed and Sealed this

Twelfth Day of April, 1994

Attest:

BRUCE LEHMAN

Attesting Officer

Commissioner of Patents and Trademarks